United States Patent
Huang et al.

(10) Patent No.: US 11,484,870 B2
(45) Date of Patent: Nov. 1, 2022

(54) ZEOLITE CATALYST FOR ALKYLATION OF TOLUENE WITH METHANOL, PREPARATION PROCESS AND USE THEREOF

(71) Applicant: Taiyuan University of Technology, Taiyuan (CN)

(72) Inventors: Wei Huang, Taiyuan (CN); Ahmad Faraz, Taiyuan (CN); Bin Wang, Taiyuan (CN); Yueli Wen, Taiyuan (CN); Chunyao Hao, Taiyuan (CN); Huijun Li, Taiyuan (CN); Yuhua Liu, Taiyuan (CN)

(73) Assignee: Taiyuan University of Technology, Taiyuan (CN)

( * ) Notice: Subject to any disclaimer, the term of this patent is extended or adjusted under 35 U.S.C. 154(b) by 0 days.

(21) Appl. No.: 16/884,544

(22) Filed: May 27, 2020

(65) Prior Publication Data

US 2021/0260565 A1 Aug. 26, 2021

(30) Foreign Application Priority Data

Feb. 20, 2020 (CN) .......................... 202010104136.2

(51) Int. Cl.
| | |
|---|---|
| *B01J 29/06* | (2006.01) |
| *B01J 29/70* | (2006.01) |
| *B01J 35/10* | (2006.01) |
| *B01J 6/00* | (2006.01) |
| *B01J 37/00* | (2006.01) |
| *C07C 4/06* | (2006.01) |
| *B01J 29/08* | (2006.01) |
| *B01J 37/02* | (2006.01) |
| *B01J 37/28* | (2006.01) |

(52) U.S. Cl.
CPC .............. *B01J 29/70* (2013.01); *B01J 6/001* (2013.01); *B01J 29/08* (2013.01); *B01J 29/082* (2013.01); *B01J 35/1014* (2013.01); *B01J 35/1019* (2013.01); *B01J 35/1023* (2013.01); *B01J 37/0036* (2013.01); *B01J 37/0201* (2013.01); *B01J 37/28* (2013.01); *C07C 4/06* (2013.01); *B01J 2029/081* (2013.01); *B01J 2229/16* (2013.01); *B01J 2229/186* (2013.01); *C07C 2529/08* (2013.01); *C07C 2529/70* (2013.01)

(58) Field of Classification Search
CPC . B01J 6/001; B01J 29/08; B01J 29/082; B01J 2029/081; B01J 2229/16; B01J 2229/186; B01J 35/1014; B01J 35/1019; B01J 35/1023; B01J 35/023; B01J 37/0036; B01J 37/0201; B01J 37/28; C07C 2529/08; C07C 2/862; C07C 2/867
USPC ...................................... 502/60, 79, 208, 214
See application file for complete search history.

(56) References Cited

U.S. PATENT DOCUMENTS

| | | | | |
|---|---|---|---|---|
| 4,491,678 | A * | 1/1985 | Oda ................. | B01J 29/04 585/466 |
| 2005/0272593 | A1* | 12/2005 | Wachter ............. | B01J 37/0232 502/60 |
| 2009/0082193 | A1* | 3/2009 | Wachter ............. | B01J 21/16 502/68 |
| 2018/0134647 | A1* | 5/2018 | Ozmeral ............ | B01J 37/0201 |

OTHER PUBLICATIONS

Mielczarski et al., "Infrared Investigations of the Alkylation of Toluene with Methanol by Alkali-Modified Zeolites", Ind. Eng. Chem. Res., 1990, 29, pp. 1579-1582.*

* cited by examiner

*Primary Examiner* — Elizabeth D Wood
(74) *Attorney, Agent, or Firm* — Andrus Intellectual Property Law, LLP

(57) ABSTRACT

The disclosure relates to a zeolite catalyst for side-chain alkylation of toluene with methanol, including a zeolite NaX and $Na_3PO_4$ or $Na_2HPO_4$ supported on the zeolite NaX. The zeolite catalyst can be effective for catalyzing the side-chain alkylation of toluene with methanol. The disclosure also relates to a process for preparing a zeolite catalyst for side-chain alkylation of toluene with methanol, which is simple, practical and cheap in cost.

8 Claims, No Drawings

ZEOLITE CATALYST FOR ALKYLATION OF TOLUENE WITH METHANOL, PREPARATION PROCESS AND USE THEREOF

CROSS-REFERENCE TO RELATED APPLICATIONS

The present application claims priority of Chinese Patent Application Publication No. CN113275032, filed on Feb. 20, 2020, the content of which is hereby incorporated by reference in its entirety.

TECHNICAL FIELD

The present invention relates generally to production of styrene by side-chain alkylation of toluene with methanol, and in particular, to a zeolite catalyst for the alkylation of toluene with methanol. Furthermore, the present invention also relates to a process for preparing the zeolite catalyst and to its use.

BACKGROUND

Styrene is an industrially important monomer that is used in the production of many polymers such as rubbers and plastics. The current process for the production of styrene requires two steps, starting with benzene alkylation with ethylene to produce ethylbenzene and followed by dehydrogenation of ethylbenzene to styrene which is an energy-intensive, endothermic and thermodynamically limited process typically operated at high temperatures (greater than 600° C.). Furthermore, this method of producing styrene from ethylbenzene imposes some major environmental problems such as emission of harmful greenhouse gases.

Side-chain alkylation of toluene with methanol is a prospective technology for achieving one-step production of styrene under minor conditions. Also, this method of producing styrene reduces greenhouse gas emissions and is relatively energy efficient.

Until now, many researchers have used different zeolite catalysts, especially CsX for the side-chain alkylation of toluene with methanol, but these catalysts are generally expensive. It is desirable that zeolite NaX which is cheap be used to catalyze the side-chain alkylation of toluene with methanol.

CN109395767A describes a $K_3PO_4$/NaX catalyst and its preparation method, including steps of: a) mixing zeolite NaX with $K_3PO_4$ solution proportionally with the mixture being stirred at 80° C. (in bath) for 2 h to obtain a solid I by suction filtration; b) adding the solid I into further $K_3PO_4$ solution with the mixture being stirred at 80° C. (in bath) for 2 h to obtain a solid II by suction filtration; and c) adding the solid II into further $K_3PO_4$ solution with the mixture being stirred at 80° C. (in bath) for 2 h to obtain a solid III by suction filtration, which is dried for 12 h and then calcinated for 3 h.

This method is complex as the zeolite NaX is required to be exchanged with $K_3PO_4$ solution three times and to be washed three times in order to prepare $K_3PO_4$/NaX catalyst.

SUMMARY

It is therefore an objective of the present invention to overcome such problems of the prior art and to provide a zeolite catalyst, which is cheap in cost and effective for catalyzing the side-chain alkylation of toluene with methanol to produce styrene, and enables a simple preparation thereof.

A first aspect of the invention relates to a zeolite catalyst for side-chain alkylation of toluene with methanol, and in particular to a $Na_3PO_4$-modified or $Na_2HPO_4$-modified zeolite NaX, referred to herein as $Na_3PO_4$/NaX or $Na_2HPO_4$/NaX, respectively.

The zeolite catalyst according to the first aspect of the present invention includes a zeolite NaX and $Na_3PO_4$ or $Na_2HPO_4$ supported on the zeolite NaX.

In some embodiments of the invention, the zeolite NaX may have a Si/Al ratio of about 1 to about 10 and a specific surface area of about 40 $m^2/g$ to about 600 $m^2/g$. In a preferred embodiment, the zeolite NaX may have a Si/Al ratio of about 1.24 and a specific surface area of about 527 $m^2/g$.

In preferred embodiments of the invention, the zeolite catalyst may have a size between 40 mesh and 60 mesh.

A second aspect of the present invention relates to a process for preparing a zeolite catalyst for side-chain alkylation of toluene with methanol, including steps of:

(1) immersing a zeolite NaX in trisodium phosphate aqueous solution ($Na_3PO_4$ aqueous solution) or dibasic sodium phosphate aqueous solution ($Na_2HPO_4$ aqueous solution) with the mixture being stirred at 60 to 90° C. for 2 h and then cooled down to room temperature;

(2) placing the cooled mixture into an oven at 60 to 90° C. to have all liquid evaporated, leaving a solid;

(3) calcinating the solid obtained in step (2) in air at 400 to 600° C. for 3 h at a heating rate of 3 K/min.

In some embodiments of the invention, the zeolite NaX may have a Si/Al ratio of about 1 to about 10 and a specific surface area of about 40 $m^2/g$ to about 600 $m^2/g$. In a preferred embodiment, the zeolite NaX may have a Si/Al ratio of about 1.24 and a specific surface area of about 527 $m^2/g$.

In some embodiments, the $Na_3PO_4$ or $Na_2HPO_4$ solution in step (1) may have a concentration of 0.01 M to 0.1 M. In preferred embodiments, the $Na_3PO_4$ or $Na_2HPO_4$ solution in step (1) may have a concentration of 0.05 M to 0.075 M, and the $Na_3PO_4$/NaX or $Na_2HPO_4$/NaX catalyst prepared by using the $Na_3PO_4$ or $Na_2HPO_4$ solution at the concentration of such a range, when used in the side-chain alkylation of toluene with methanol to produce styrene, enables a selectivity and yield of both ethylbenzene and styrene to be each up to over 60% and a yield of styrene to be at least about 91% higher than that provided by the $K_3PO_4$/NaX catalyst.

In preferred embodiments, the temperature in step (1) may be 80° C.

In preferred embodiments, in step (2), the cooled mixture may be kept in the oven at 60 to 90° C. for 16 to 18 h to be subjected to an evaporation.

In preferred embodiments, the calcination temperature in step (3) may be 500° C.

In preferred embodiments, the process may further include crushing, pelletizing and sieving the calcinated solid to obtain the zeolite catalyst with a size between 40 mesh and 60 mesh.

The zeolite catalyst for the side-chain alkylation of toluene with methanol of the invention can be prepared by using the cheap zeolite NaX as a source material and only $Na_3PO_4$ or $Na_2HPO_4$ as a zeolite modifying ingredient, and the process for preparing the zeolite catalyst according to the present invention is simple and practical. These lead to a low cost of the raw material of the zeolite catalyst and a low production cost.

Compared with the process for preparing the K$_3$PO$_4$/NaX catalyst described in CN109395767A, which requires the zeolite NaX to be exchanged with K$_3$PO$_4$ solution three times and to be washed three times, the process for preparing the Na$_3$PO$_4$/NaX or Na$_2$HPO$_4$/NaX catalyst according to the present invention is more simple as it involves only one immersion step and only one evaporation step.

In addition, it appears from our studies that the life of the Na$_3$PO$_4$/NaX or Na$_2$HPO$_4$/NaX catalyst of the invention can be longer than that of the K$_3$PO$_4$/NaX catalyst.

DETAILED DESCRIPTION

The zeolite catalyst for the side-chain alkylation of toluene with methanol and the process for preparing the same, according to the present invention, will now be described in more detail by reference to the following examples, which are illustrative only and do not limit the scope of the invention.

Example 1

10 g of zeolite NaX (Catalyst Plant of Nankai University, Si/Al=1.24, with a specific surface area of 527 m$^2$/g) was added into 100 mL aqueous solution of Na$_3$PO$_4$.12H$_2$O (0.01 M). After stirring for 2 h at 80° C., the solution was kept for some time at room temperature to cool down. This solution cooled down was kept in an oven at 80° C. without filtration for about 17 h to evaporate all the liquid inside, leaving behind a solid. This solid obtained was then calcinated in air for 3 h at 500° C. at a heating rate of 3K/min. The resulting powder was crushed, pelletized and sieved to obtain the zeolite catalyst with a size between 40 mesh and 60 mesh.

Examples 2-5

Examples 2-5 were identical to Example 1, but with the difference that the concentration of the aqueous solution of Na$_3$PO$_4$.12H$_2$O as used in Examples 2-5 was 0.025 M, 0.05 M, 0.075 M and 0.1 M, respectively.

Example 6

The catalysts prepared in Examples 1-5 above were tested for their catalytic performance for side-chain alkylation of toluene with methanol in a fixed bed reactor at atmospheric pressure.

1.2 g of the catalyst was placed in the middle of a stainless-steel tube having an inner diameter of 7 mm, and the catalyst was supported by quartz sands at an outlet of the reaction tube, and separated by quartz cotton in the middle. Nitrogen was used as a carrier gas, a flow rate was 10.0 ml/min, a molar ratio of toluene to methanol was 5:1, and a mass space velocity was 1.0 h$^{-1}$. The catalyst was activated at 450° C. for 2 h under atmospheric nitrogen atmosphere and then lowered to 425° C. for evaluation. To prevent the reaction gases from being condensed, a heating belt was wrapped around from the reactor to a six-way valve to keep a temperature of about 200° C., and a auxiliary furnace was also equipped to keep the temperature from the six-way valve to a chromatographic injector at 200° C.

Reaction products were quantitatively analyzed online by Haixin GC950 gas chromatograph equipped with HP-FFAP column (0.53 mm×50 m) and the products were detected by a hydrogen flame ionization detector (FID). Measurement conditions of the gas chromatograph were as follows: column furnace temperature: 70° C., detector temperature: 220° C., gasification chamber temperature: 200° C., air partial pressure: 0.05 MPa, hydrogen partial pressure: 0.12 MPa, carrier gas flow rate: 35 ml/min, and gas injection volume: 0.1 ml/h. The products were quantified by the area correction normalization method. Since an excess of toluene in the reaction system was used, product selectivity and yield were calculated based on methanol.

Table 1 below presents the results of the catalyst evaluation in Example 6, comparing methanol conversion and a selectivity and yield for each of ethylbenzene and styrene as well as a yield for both of them, provided by the five catalysts prepared in Example 1-5 using a feed composition of toluene and methanol in a molar ratio of 5:1 at a mass space velocity of 1.0 h$^{-1}$, a nitrogen flow rate of 10 ml/min and at a reaction temperature of 425° C.

TABLE 1

Performance of Catalyst

| | | Selectivity (%) | | Yield (%) | | |
|---|---|---|---|---|---|---|
| Example | MET Conv. % | $S_{EB}$ | $S_{STY}$ | $Y_{EB}$ | $Y_{STY}$ | $Y_{(EB + STY)}$ |
| 1 | 100 | 41.2 | 1.3 | 41.2 | 1.3 | 42.5 |
| 2 | 99.8 | 29.4 | 4.2 | 29.3 | 4.2 | 33.5 |
| 3 | 100 | 48.4 | 16.6 | 48.3 | 16.6 | 64.9 |
| 4 | 99.9 | 45.6 | 15.3 | 45.5 | 15.3 | 60.9 |
| 5 | 100 | 22.1 | 3.6 | 22.1 | 3.6 | 25.7 |

As apparent from the results of Table 1, the Na$_3$PO$_4$/NaX catalyst according to the embodiments of the invention can be effective for catalyzing the side-chain alkylation of toluene with methanol. Surprisingly, the Na$_3$PO$_4$/NaX catalyst prepared by using a Na$_3$PO$_4$ solution at a concentration of about 0.05 M to about 0.075 M, enables a selectivity and yield for both ethylbenzene and styrene to be each up to over 60%, and the yield of styrene to be much higher, in particular at least 91% higher, than that provided by the K$_3$PO$_4$/NaX catalyst described in CN 103935767 A.

In addition it was found that results similar to those achieved by the Na$_3$PO$_4$/NaX catalysts mentioned above were obtained with Na$_2$HPO$_4$/NaX catalysts prepared by using Na$_2$HPO$_4$ solution at a concentration of 0.01 M to 0.1 M when used in the side-chain alkylation of toluene with methanol to produce styrene.

The present invention has been described in detail by reference to the specific embodiments. It will be apparent that modifications and variations are possible without departing from the scope of the invention which is defined in the appended claims.

What is claimed is:

1. A zeolite catalyst for side-chain alkylation of toluene with methanol, comprising a zeolite NaX and Na$_3$PO$_4$ or Na$_2$HPO$_4$ supported on the zeolite NaX, wherein the zeolite catalyst for side-chain alkylation of toluene with methanol is prepared by the process of:
   a. immersing the zeolite NaX in Na$_3$PO$_4$ aqueous solution or Na$_2$HPO$_4$ aqueous solution with the mixture being stirred at 60 to 90° C. for 2 h and then cooled down to room temperature;
   b. placing the cooled mixture into an oven at 60 to 90° C. to have all liquid evaporated, leaving a solid; and
   c. calcinating the solid obtained in step b in air at 400 to 600° C. for 3 h at a heating rate of 3 K/min;
   wherein the Na$_3$PO$_4$ aqueous solution or the Na$_2$HPO$_4$ aqueous solution in step a has a concentration of 0.05 M to 0.075 M;

wherein side-chain alkylation of toluene with methanol with the zeolite catalyst under conditions of a feed molar ratio of toluene to methanol of 5:1, a mass space velocity of 1.0 $h^{-1}$, a nitrogen flow rate of 10 ml/min, and a reaction temperature of 425° C., yields styrene in a range of 15.3-16.6%.

2. A zeolite catalyst according to claim 1, wherein the zeolite NaX has a Si/Al ratio of 1 to 10 and a specific surface area of 40 $m^2$/g to 600 $m^2$/g.

3. A zeolite catalyst according to claim 2, wherein the zeolite NaX has a Si/Al ratio of 1.24 and a specific surface area of 527 $m^2$/g.

4. A zeolite catalyst according to claim 1, wherein the zeolite catalyst has a size between 40 mesh and 60 mesh.

5. A zeolite catalyst according to claim 1, wherein the calcination temperature in step c is 500° C.

6. A zeolite catalyst according to claim 1, wherein the process further comprises crushing, pelletizing and sieving the calcinated solid to obtain the zeolite catalyst with a size between 40 mesh and 60 mesh.

7. A zeolite catalyst according to claim 1, wherein in step a the temperature is 80° C.

8. A zeolite catalyst according to claim 1, wherein in step b the cooled mixture is kept in the oven at 60 to 90° C. for 16 to 18 h to be subjected to an evaporation.

* * * * *